United States Patent [19]

Schuster et al.

[11] Patent Number: 4,903,481
[45] Date of Patent: Feb. 27, 1990

[54] DEVICE FOR PROTECTING A LAMBDA PROBE

[75] Inventors: Hans-Dieter Schuster, Schorndorf; Gottfried Wollenhaupt, Stuttgart, both of Fed. Rep. of Germany

[73] Assignee: Daimler-Benz Aktiengesellschaft, Stuttgart, Fed. Rep. of Germany

[21] Appl. No.: 286,164

[22] Filed: Dec. 19, 1988

[30] Foreign Application Priority Data

Dec. 19, 1987 [DE] Fed. Rep. of Germany ....... 3743295

[51] Int. Cl.⁴ .............................................. G01N 27/58
[52] U.S. Cl. ........................................ 60/276; 204/428
[58] Field of Search ........................... 60/276; 204/428

[56] References Cited

U.S. PATENT DOCUMENTS

| | | | |
|---|---|---|---|
| 4,240,890 | 12/1980 | Watanabe | 204/428 |
| 4,362,605 | 12/1982 | Bozon | 60/276 |
| 4,484,440 | 11/1984 | Oki et al. | |
| 4,617,795 | 10/1986 | Abthoff | 60/276 |

FOREIGN PATENT DOCUMENTS

| | | |
|---|---|---|
| 2319859 | 11/1973 | Fed. Rep. of Germany . |
| 2348505 | 4/1975 | Fed. Rep. of Germany ...... 204/428 |
| 2937089 | 3/1980 | Fed. Rep. of Germany . |
| 2937105 | 3/1980 | Fed. Rep. of Germany . |
| 3023337 | 1/1982 | Fed. Rep. of Germany . |

Primary Examiner—Douglas Hart
Attorney, Agent, or Firm—Barnes & Thornburg

[57] ABSTRACT

Thermal shock reactions of a heated lambda probe owing to the impact of liquid droplets on the heated ceramic probe body during cold starting, which phenomenon can lead to a fracture of the ceramic probe body, are avoided, and a better representativeness of the signals transmitted by the lambda probe is achieved, in that a gas deflector plate is arranged before the lambda probe in the exhaust gas flow, as seen in the direction of flow of the exhaust gases, in such a way that the lambda probe lies in its Lee.

8 Claims, 1 Drawing Sheet

DEVICE FOR PROTECTING A LAMBDA PROBE

BACKGROUND AND SUMMARY OF THE INVENTION

An object of the invention is to provide a device for prolonging the service life and improving the representativeness of the measurements of a heated lambda probe arranged in the exhaust gas flow of an internal combustion engine.

Lambda probes determine the residual oxygen content in the engine exhaust gas, and thereby facilitate a precise control of the air/fuel mixture, so that the resulting engine exhaust gas can be optimally converted at an exhaust gas catalytic converter. The construction of lambda probes is well known to the expert, and described in detail in, for example, German Published Unexamined Patent Application (DOS) 3,023,337. Lambda probes consist in general of a solid electrolyte tube, closed at one side and projecting into the exhaust gas flow, which carries the measuring electrode on its outside and the reference electrode on its inside. The solid electrolyte tube consists of ceramics and projects into the exhaust gas flow during measurement. For protection against contact with liquid drops and particles of solid materials, the solid electrolyte tube is surrounded by a protective sleeve, which has openings for the inlet of the gases to the solid electrolyte tube. Thus, there is known, for example from German Published Unexamined Patent Application (DOS) 2,937,105, a lambda probe with a protective sleeve, which is provided with gas inlet openings on the floor side. The admittance of particles to the probe is prevented by a plate, which is arranged at the protective sleeve before the openings parallel to the floor of the protective sleeve, and serves as particle trap. However, to activate the particle trap requires an expensive alignment of the lambda probe to the gas flow.

Since the lambda probe starts to deliver readings only from a relatively high temperature of the solid electrolyte, it is provided with a heater for the solid electrolyte tube, which heats the solid electrolyte tube to temperatures of approximately 600°–800° C. In this way, it is possible to obtain measurement results immediately after the engine has been started. The rapid heating up of the ceramic body (solid electrolyte tube) to the operating temperature within from 20 to 30 sec. does, however, entail disadvantages. After the engine has been cold-started, condensation of the exhaust gas takes place at the cold exhaust pipes and at any upstream primary catalytic converters with metal support matrix. By impacts on the heated-up ceramic body, the larger drops of this cold condensate, which consists largely of water, cause thermal shock reactions, which cause a fracture of the ceramics, and thus the destruction of the lambda probe.

In order to improve the performance characteristics of the engines, or because of structural factors (V-engines), the exhaust gas pipes of individual cylinders or cylinder assemblies are not united until immediately before the location of installation of the lambda probe. By virtue of the production tolerances both in the air-intake region and also for cylinders and pistons and the fuel metering, slight dispersions occur in the exhaust gas composition of individual cylinders of cylinder assemblies. With an exhaust gas pipe routing, in which the exhaust gas pipes of the individual cylinders or cylinder assemblies are not united until immediately before the location of the installation of the lambda probe, it can therefore happen that during the exhaust gas sensing by the lambda probe individual cylinders or cylinder groups are measured preferentially. The reading transmitted by the lambda probe is then no longer representative for all cylinders, but can cause a misinterpretation of the true exhaust gas composition. Consequently, the air/fuel mixture is no longer controlled to the optimum lambda value, which has a negative effect on the exhaust emission, in a known way.

It is therefore an object of the invention to find a device with which both the service life of the lambda probe as such, and also the representativeness of its measurements can be improved.

This object is achieved by providing an arrangement wherein a device is provided for prolonging the service Life and improving the representativeness of the measurements of a heated lambda probe arranged in the exhaust gas flow of an internal combustion engine, comprising a gas deflector plate arranged before the lambda probe in the exhaust gas flow, as seen in the direction of flow of the gases, in such a way that the lambda probe lies in its lee.

The device therefore consists in a gas deflector plate arranged before the lambda probe in the exhaust gas flow, as seen in the direction of flow of the gases, in such a way that the lambda probe lies in its lee. Because of the considerably greater inertia of the water drops, these fly past the probe, and do not reach the sensitive ceramic probe body. In addition, because of the eddies occasioned by the stalling of the flow at the plate, the arrangement of the gas deflector plate immediately before the lambda probe causes an improvement of the exhaust gas mixing, and thereby a representative probe signal for the lambda control.

The gas deflector plate is, of course, to represent as low as possible a drag for the exhaust gas flow. Consequently, preference is given to a finger-shaped gas deflector plate reaching into the gas flow before the lambda probe, which has a width of 80 to 180% of the basket guard diameter of the lambda probe, and is arranged approximately 5 to 30 mm before the lambda probe. The further the gas deflector plate is arranged before the lambda probe, the wider it must become. Since the length of the lee depends not only on the width of the gas deflector plate, but also on the geometrical relationships of the exhaust gas run, and also on the rate of gas flow, it is expedient to determine the optimum dimensions experimentally, which is possible for an expert without difficulty. With the presently customary embodiments of lambda probes, and also with the presently customary layout of the exhaust gas run, the optimum values for the width of the gas deflector plate lie approximately between 10.5 and 13.5 mm, which corresponds to 90 to 110% of the basket guard diameter, and the separation of the gas deflector plate to the probe amounts to approximate 15 to 25 mm. If the gas deflector plate becomes too wide, the result is an additional drag in the exhaust gas flow, which is undesirable.

The length of the gas deflector plate is to amount to approximately the length of the part of the lambda probe reaching in to the exhaust gas flow, so that the lambda probe certainly also lies in the lee. However, it has emerged that even with a somewhat shorter gas deflector plate, results which are still satisfactory can be achieved. A gas deflector plate, whose length exceeds the length of the part of the lambda probe reaching into the exhaust gas flow, has no damaging effect on the function, but does, of course, represent a larger drag. This larger drag can be tolerated, however, if a simplified mounting of the gas deflector plate is thereby rendered possible, for example in that the gas deflector plate entirely pierces the exhaust gas pipe. However, it is preferred to dimension the length of the gas deflector plate so that it amounts to 80 to 120% of the length of the part of the lambda probe reaching into the exhaust gas flow. To reduce the drag it is advantageous if the gas deflector plate receives a streamlined form, for example in that it receives a form backswept against the exhaust gas flow, or if it is formed convexly, as seen in the direction of flow of the gases.

Other objects, advantages and novel features of the present invention will become apparent from the following detailed description of the invention when considered in conjunction with the accompanying drawings.

DETAILED DESCRIPTION OF THE DRAWINGS

Figure 1:
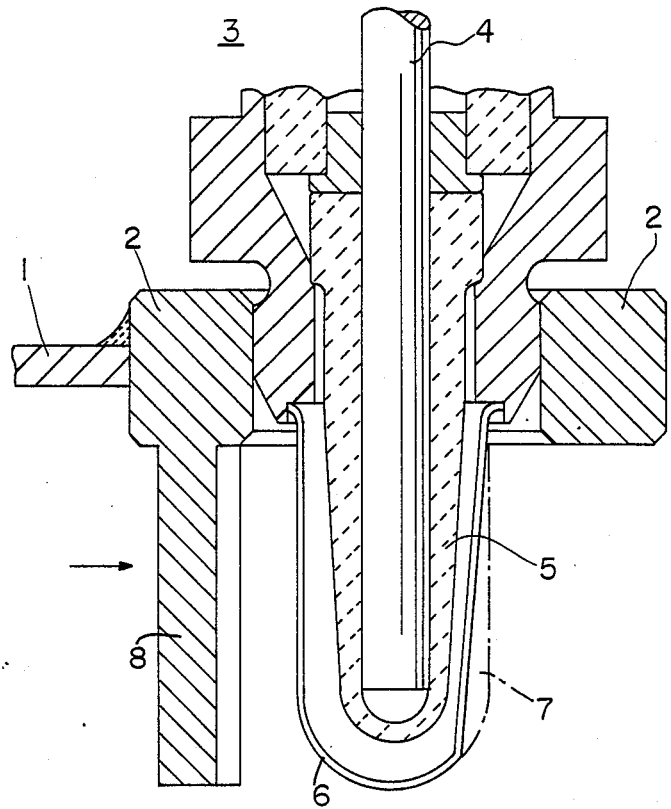
FIG. 1 shows, in magnified form, a partial longitudinal section through an exhaust gas pipe with deflector plate and lambda probe constructed in accordance with a preferred embodiment of the present invention.
Figure 2:
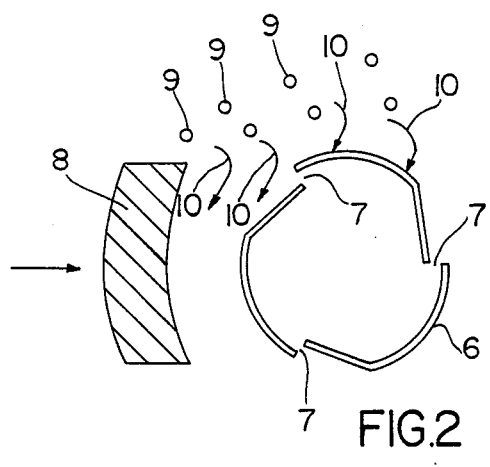
FIG. 2 shows a schematic cross-section through the deflector plate and the basket guard of the probe of the FIG. 1 arrangement.

Welded into the wall of the exhaust gas pipe 1 is the well 2, which is provided with an internal thread, into which the lambda probe 3 is screwed. Recognizable in the lambda probe 3 are the heating rod 4, the ceramic solid electrolyte 5 and the basket guard 6 of the probe with gas inlet slots 7. Located before the lambda probe in the direction of flow of the exhaust gas, which is represented by the arrow, is the gas deflector plate 8 which, in this case, is part of the thread well 2. However, it is also contemplated to mount the gas deflector plate separately in the exhaust gas pipe according to other preferred embodiments of the invention. To reduce the drag, the gas deflector plate 8 is formed convexly, as seen in the direction of flow of the exhaust gas. As becomes clear in FIG. 2, the water droplet 9 located in the exhaust gas fly past the lambda probe lying in the lee of the gas deflector plate 8, while the exhaust gas, as represented by the arrows 10, is strongly swirled behind the gas deflector plate, and can approach the ceramic probe body through the gas inlet slots 7.

It is achieved with the invention that the ceramic probe body can no longer crack through thermal shock reactions resulting from the impact of water droplets on the heated ceramics, and that the exhaust gas is very well provided with eddies by the gas deflector plate, so that a better representativeness of the reading transmitted by the lambda is achieved.

Although the present invention has been described and illustrated in detail, it is to be clearly understood that the same is by way of illustration and example only, and is not to be taken by way of limitation. The spirit and scope of the present invention are to be limited only by the terms of the appended claims.

What is claimed:

1. Device for prolonging the service life and improving the representativeness of the measurements of a heated lambda probe arranged in the exhaust gas flow of an internal combustion engine, wherein a gas deflector plate means is arranged upstream of and separated from the lambda probe in the exhaust gas flow as seen in the direction of flow of the exhaust gases, for deflecting the exhaust gas and water particles therein, and wherein the lambda probe is located in a lee of the exhaust gas deflector plate means and downstream thereof whereby the lambda probe is protected from impingement of the water particles in the exhaust gas which are deflected sufficiently to pass by the probe.

2. Device according to claim 1, wherein the gas deflector plate means has a width of 80 to 180% of a basket guard diameter of the lambda probe, and is arranged 5 to 30 nm before the lambda probe.

3. Device according to claim 1, wherein the length of the gas deflector plate means amounts to 80 to 120% of the length of the part of the lambda probe reaching into the exhaust gas flow.

4. Device according to claim 1, wherein the gas deflector plate means is formed convexly, as seen in the direction of flow of the exhaust gases.

5. Device according to claim 2, wherein the length of the gas deflector plate means amounts to 80 to 120% of the length of the part of the lambda probe reaching into the exhaust gas flow.

6. Device according to claim 2, wherein the gas deflector plate means is formed convexly, as seen in the direction of flow of the exhaust gases.

7. Device according to claim 3, wherein the gas deflector plate means is formed convexly, as seen in the direction of flow of the exhaust gases.

8. Device according to claim 5, wherein the gas deflector plate means is formed convexly, as seen in the direction of flow of the exhaust gases.

* * * * *